US008194067B2

(12) United States Patent
Raby et al.

(10) Patent No.: US 8,194,067 B2
(45) Date of Patent: Jun. 5, 2012

(54) PLANAR GUIDES TO VISUALLY AID ORTHODONTIC APPLIANCE PLACEMENT WITHIN A THREE-DIMENSIONAL (3D) ENVIRONMENT

(75) Inventors: Richard E. Raby, North St. Paul, MN (US); Nicholas A. Stark, Cottage Grove, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 422 days.

(21) Appl. No.: 10/771,641

(22) Filed: Feb. 4, 2004

(65) Prior Publication Data

US 2005/0170309 A1 Aug. 4, 2005

(51) Int. Cl.
*G06T 17/00* (2006.01)
*A61C 7/00* (2006.01)
(52) U.S. Cl. ........... 345/420; 433/24; 345/419; 345/679
(58) Field of Classification Search .................... 433/24, 433/215; 345/419, 420, 679
See application file for complete search history.

(56) References Cited

U.S. PATENT DOCUMENTS

| | | | |
|---|---|---|---|
| 4,014,096 A | 3/1977 | Dellinger | |
| 4,455,137 A | 6/1984 | Diamond | |
| 4,850,864 A | 7/1989 | Diamond | |
| 5,011,405 A | 4/1991 | Lemchen | |
| 5,015,180 A | 5/1991 | Randklev | |
| 5,172,809 A | 12/1992 | Jacobs et al. | |
| 5,354,199 A | 10/1994 | Jacobs et al. | |
| 5,429,229 A | 7/1995 | Chester et al. | |
| 5,431,562 A | 7/1995 | Andreiko et al. | |
| 5,583,977 A * | 12/1996 | Seidl | 345/619 |
| 5,588,098 A * | 12/1996 | Chen et al. | 345/653 |
| 5,605,459 A | 2/1997 | Kuroda et al. | |
| 5,712,965 A * | 1/1998 | Fujita et al. | 345/419 |
| 6,123,544 A | 9/2000 | Cleary | |
| 6,334,772 B1 * | 1/2002 | Taub et al. | 433/24 |
| 6,448,964 B1 * | 9/2002 | Isaacs et al. | 345/419 |
| 6,898,302 B1 | 5/2005 | Brummer | |
| 7,029,275 B2 | 4/2006 | Rubbert et al. | |

(Continued)

FOREIGN PATENT DOCUMENTS

EP 1041939 5/2003

(Continued)

OTHER PUBLICATIONS

Visualization in biomedical computing, Richard A. Robb, Parallel Computing 25 (1999) 2067-2110.

(Continued)

*Primary Examiner* — Todd Manahan
*Assistant Examiner* — Michael R Ballinger

(57) ABSTRACT

Techniques are described for providing an environment for modeling and depicting a three-dimensional (3D) representation of a patient's dental arch to assist practitioners in orthodontic diagnosis and treatment. A system is described, for example, that includes modeling software executing on a computing device to provide a three-dimensional (3D) environment. The modeling software includes a rendering engine that renders a digital representation of a dental arch within the 3D environment, and a user interface that displays a planar guide within the 3D environment as a visual aid to a practitioner in the placement of an orthodontic appliance relative to the dental arch. By interacting with the system, orthodontic practitioners are able to visualize the 3D representation of the dental arch, and precisely position "virtual" orthodontic appliances relative to the modeled dental arch.

89 Claims, 10 Drawing Sheets

U.S. PATENT DOCUMENTS

| | | |
|---|---|---|
| 7,033,327 B2 | 4/2006 | Raby |
| 7,080,979 B2 | 7/2006 | Rubbert et al. |
| 7,188,421 B2 | 3/2007 | Cleary et al. |
| 2002/0025503 A1 | 2/2002 | Chapoulaud et al. |
| 2002/0028417 A1 | 3/2002 | Chapoulaud et al. |
| 2002/0156652 A1 | 10/2002 | Sachdeva et al. |
| 2002/0180760 A1 | 12/2002 | Rubbert et al. |
| 2003/0096210 A1 | 5/2003 | Rubbert et al. |
| 2003/0143509 A1 | 7/2003 | Kopelman |
| 2003/0152884 A1* | 8/2003 | Wiechmann et al. ............ 433/9 |
| 2003/0215764 A1 | 11/2003 | Kopelman et al. |
| 2003/0224316 A1* | 12/2003 | Marshall ........................ 433/24 |
| 2004/0096799 A1 | 5/2004 | Hughes et al. |
| 2004/0115586 A1 | 6/2004 | Andreiko |
| 2004/0142297 A1 | 7/2004 | Taub et al. |
| 2004/0197727 A1 | 10/2004 | Sachdeva et al. |
| 2004/0214128 A1 | 10/2004 | Sachdeva et al. |
| 2005/0033160 A1 | 2/2005 | Yamagata et al. |
| 2005/0191593 A1 | 9/2005 | Knopp |

FOREIGN PATENT DOCUMENTS

| | | |
|---|---|---|
| JP | 8-168498 | 7/1996 |
| JP | 8-280715 | 10/1996 |
| JP | 2001-517533 | 9/2001 |
| JP | 2002-500054 | 1/2002 |
| JP | 2002-514465 | 5/2002 |
| JP | 2003-532485 | 11/2003 |
| WO | WO 97/03622 | 2/1997 |
| WO | WO 98/53428 | 11/1998 |
| WO | WO 99/16380 | 4/1999 |
| WO | WO 99/34747 | 7/1999 |
| WO | WO 01/47405 | 7/2001 |
| WO | WO 01/80761 | 11/2001 |
| WO | WO 02/24100 | 3/2002 |
| WO | WO 03/061507 | 7/2003 |
| WO | WO 03/073382 | 9/2003 |

OTHER PUBLICATIONS

Anatomy Browser: A novel approach to visualization and integration of medical information; Golland et al., Computer Assisted Surgery, 4:129-143, 1999.

User Controlled Overviews of an image Library: A Case Study of the Visible Human; North et al., Human-Computer Interaction Laboratory, Department of Computer Science, Institute for Systems Research, University of Maryland, 1996, pp. 74-82.

* cited by examiner

PLANAR GUIDES TO VISUALLY AID ORTHODONTIC APPLIANCE PLACEMENT WITHIN A THREE-DIMENSIONAL (3D) ENVIRONMENT

TECHNICAL FIELD

The invention relates to electronic orthodontics and, more particularly, computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances, known as brackets, that are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly from one appliance to the next in accordance with the patient's malocclusions. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

As can be appreciated, it is important for the practitioner using straight wire appliances to fix each bracket in the exact proper position on the corresponding tooth. If, for example, a bracket is placed too high in an occlusal direction on the tooth surface, the archwire will tend to position the crown of the tooth too close to the gingiva (gums) at the end of the treatment. As another example, if the bracket is placed to one side of the center of the tooth in either the mesial or distal directions, the resultant tooth orientation will likely be an orientation that is excessively rotated about its long axis.

The process of positioning and bonding the brackets to the patient's teeth requires considerable care, and requires the practitioner to visually determine the proper location of the brackets on the respective teeth. Often, a practitioner determines bracket positions by the use of a ruler, protractor and pencil to measure and mark features on a plaster cast made from impressions of the patient's teeth. This process is often difficult to carry out with precision, and may be subjective in nature. Consequently, it is often difficult for the practitioner to ensure that the brackets are precisely positioned on the teeth at correct locations.

SUMMARY

In general, the invention relates to techniques for assisting practitioners in orthodontic diagnosis and treatment. More specifically, a system is described that provides an environment for modeling and depicting a three-dimensional (3D) representation of a patient's dental arch. By interacting with the system, orthodontic practitioners are able to visualize the 3D representation of the dental arch, and precisely position "virtual" orthodontic appliances relative to the modeled dental arch. For example, the orthodontic practitioner may interact with the system to position brackets on one or more teeth within the modeled dental arch.

As described in detail herein, the system presents planar guides within the 3D environment to visually aid the practitioner in the placement and adjustment of the brackets relative to their respective teeth. In practice, the planar guides are located in a coordinate system associated with the bracket currently being positioned or adjusted. As a result, the system automatically moves the planar guides as the practitioner moves the bracket with respect to the tooth within the 3D environment. Consequently, the planar guides provide a good visual indication of the position of the bracket relative to the tooth on which the bracket is being placed.

Each planar guide may be visually represented as a semi-transparent two-dimensional plane within the 3D environment. This property aids the practitioner in achieving tangency between the planar guide and the surface of the tooth, thereby aiding the practitioner in placing the bracket associated with the planar guide. For example, the planar guide may assist the practitioner in visually determining the distance between the planar guide and other objects within the 3D environment, e.g., a surface of the tooth. In addition, the planar guide assists the practitioner in visualizing any portion of the tooth that may be penetrating the two-dimensional plane.

The system may be capable of displaying one or more types of planar guides. For example, two types of planar guides include: (1) a mesial planar guide, and (2) a distal planar guide. These two planar guides are rendered parallel to, and optionally equidistant from, the midsagittal plane of the bracket being placed. A third type of planar guide is an occlusal planar guide that is rendered parallel to the midlateral plane or slot of the bracket and proximate to the occlusal surface of the tooth. A fourth type of planar guide is a gingival planar guide rendered parallel to the midlateral plane or slot of the bracket and proximate to the gingival edge of the tooth.

Use of two or more of these planar guides allows the practitioner to precisely position and orient a bracket on a tooth by effectively "framing" the tooth. For example, the practitioner may align the bracket with the tooth by either aligning the mesial and distal planar guides parallel to the perceived midsagittal plane of the tooth or by aligning the occlusal planar guide with the desired occlusal plane of the dental arch.

Another exemplary type of planar guide is a midlateral planar guide that is rendered parallel to the midlateral plane of the bracket being placed. Similarly, a midfrontal planar guide may be rendered parallel to the midfrontal plane of the bracket, and a midsagittal planar guide may be rendered parallel to a midsagittal plane of the bracket. Rather than being used to "frame" the tooth, however, the midlateral planar guide, midfrontal planar guide, and midsagittal planar guides may be useful in dissecting the tooth and visualizing cross-sections of the tooth.

In one embodiment, the invention is directed to a method comprising rendering a digital representation of a dental arch within a three-dimensional (3D) environment, and displaying a planar guide within the 3D environment as a visual aid to a practitioner in the placement of an orthodontic appliance relative to the dental arch.

In another embodiment, the invention is directed to a system comprising a computing device, and modeling software executing on the computing device to provide a three-dimensional (3D) environment. The modeling software comprises a rendering engine that renders a digital representation of a dental arch within the 3D environment, and a user interface that displays a planar guide within the 3D environment as a visual aid to a practitioner in the placement of an orthodontic appliance relative to the dental arch.

In another embodiment, the invention is directed to a computer-readable medium containing instructions. The instructions cause a programmable processor to render a digital representation of a tooth within a three-dimensional (3D) environment; and display a planar guide within the 3D environment as a visual aid to a practitioner in the placement of an orthodontic appliance relative to the tooth.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
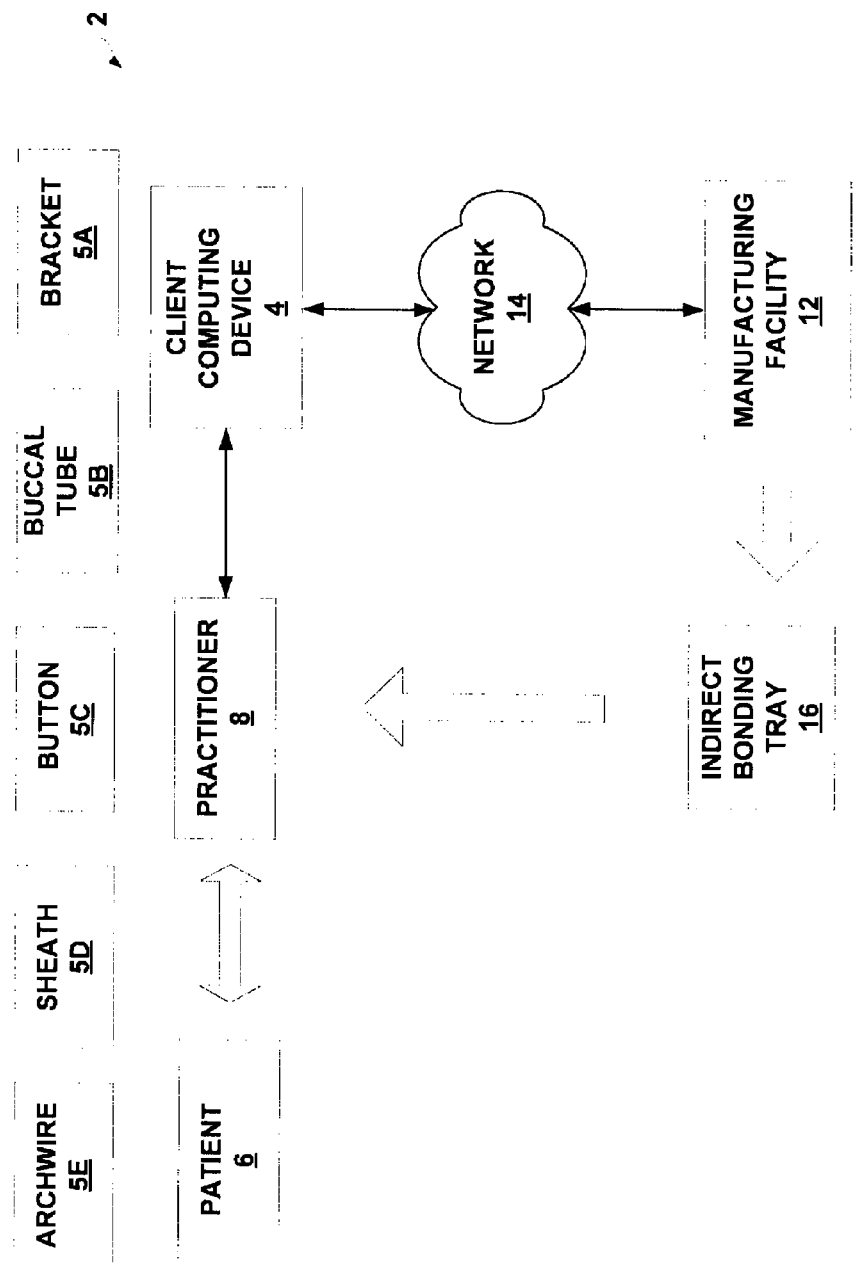
FIG. 1 is a block diagram illustrating an exemplary computer environment in which a client computing device presents one or more planar guides in a three-dimensional (3D) environment to assist a practitioner in positioning and orienting orthodontic appliances on a dental arch.

FIG. 1 is a block diagram illustrating an exemplary computer environment 2 in which a client computing device 4 presents an environment for modeling a three-dimensional (3D) representation of a dental arch of patient 6. Orthodontic practitioner 8 interacts with modeling software executing on client computer device 4 to visualize the 3D representation of the dental arch, and precisely position "virtual" brackets 5A on individual teeth within the modeled dental arch.

The 3D representation of the dental arch may be initially generated by digitally scanning a physical dental impression of the teeth of patient 6. Alternatively, practitioner 8 may use an intraoral scanner to produce the 3D digital representation directly from the teeth of patient 6. Practitioner 8 interacts with the modeling software to view the 3D digital representation of the teeth and select the point on each tooth where the respective bracket is to be located. During this process, the modeling software manipulates each bracket as a separate object within the 3D environment, and fixes the position of each bracket within the 3D space relative to a coordinate system associated with the bracket's respective tooth. Consequently, practitioner 8 is able to independently view and precisely locate each bracket within the 3D environment relative to its respective tooth.

As described in detail herein, the modeling software presents planar guides to visually aid practitioner 8 in the placement and adjustment of the brackets 5A within the 3D environment relative to their respective teeth. Each planar guide may be visually represented as a semi-transparent two-dimensional plane. The modeling software generates the planar guides within the 3D environment based on a coordinate system associated with the bracket currently being positioned or adjusted by practitioner 8. As a result, the modeling software automatically adjusts the 3D location and orientation of the planar guides as the practitioner adjusts the bracket with respect to the tooth. Consequently, the planar guides provide a good visual indication of the position of the bracket relative to the tooth on which the bracket is being placed. The techniques may readily be applied to positioning and orienting other types of orthodontic appliances relative to teeth or other regions of a dental arch. For example, the techniques may readily be used to assist a practitioner in placing, positioning, forming or otherwise designing a wide variety of appliances, such as buccal tubes 5B, buttons 5C, sheaths 5D, arch wires 5E, and other orthodontic appliances.

Once practitioner 8 has placed the brackets and indicated his or her approval, client computing device 4 communicates the bracket placement positions to manufacturing facility 12 via network 14. In response, manufacturing facility constructs an indirect bonding tray 16 for use in physically placing brackets on the teeth of patient 6. In other words, manufacturing facility 12 fabricates indirect bonding tray 16 based on the bracket placement positions selected by practitioner 8 within the 3D environment presented by client computing device 4. Manufacturing facility 12 may, for example, use conventional commercially-available brackets selected by practitioner 8 to form indirect bonding tray 16. Manufacturing facility 12 forwards indirect bonding tray 16 to practitioner 8 for use in a conventional indirect bonding procedure to place the brackets on the teeth of patient 6.

Alternatively, client computing device 4 need not forward the bracket placement positions to manufacturing facility 12. Client computing device 4 may instead output, e.g., display or print, the relevant distances and angles for each bracket to assist practitioner 8 in manually positioning the brackets on the teeth of patient 6.

Figure 2:
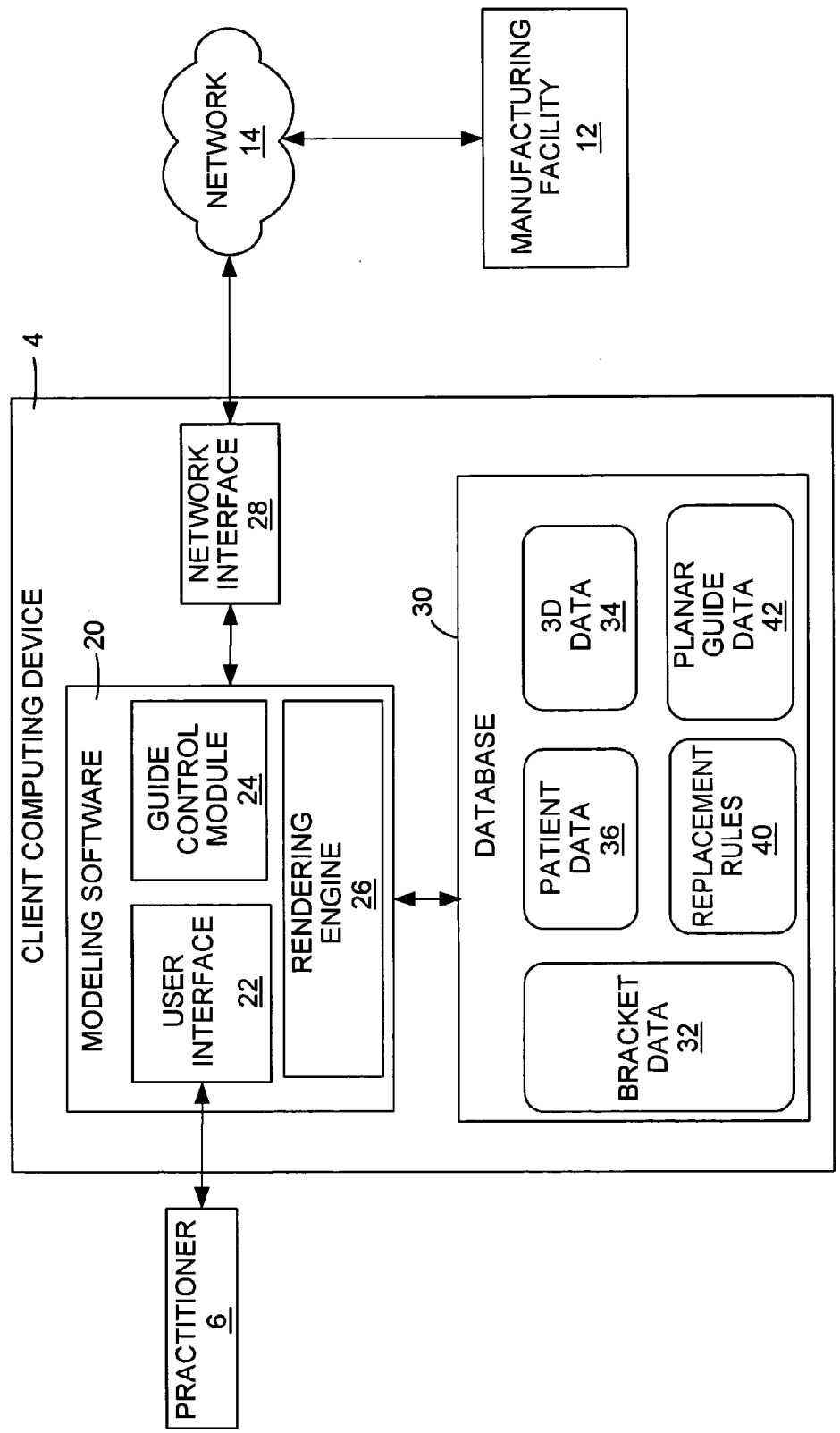
FIG. 2 is a block diagram illustrating an example embodiment of the client computing device of FIG. 1 in further detail.

FIG. 2 is a block diagram illustrating an example embodiment of client computing device 4 in further detail. In the illustrated embodiment, client computing device 4 provides an operating environment for modeling software 20. As described above, modeling software 20 presents a modeling environment for modeling and depicting the 3D representation of the teeth of patient 6 (FIG. 1). In the illustrated embodiment, modeling software 20 includes a user interface 22, a guide control module 24, and a rendering engine 26.

User interface 22 provides a graphical user interface (GUI) that visually displays the 3D representation of the patient's teeth, as well as 3D representations of the brackets and the planar guides. In addition, user interface 22 provides an interface for receiving input from practitioner 8, e.g., via a keyboard and a pointing device, for manipulating the brackets and placing the brackets on respective teeth within the modeled dental arch.

Modeling software 20 interacts with database 30 to access a variety of data, such as bracket data 32, 3D data 34, patient data 36, placement rules 40 and planar guide data 42. Database 30 may be represented in a variety of forms including data storage files, lookup tables, or a database management system (DBMS) executing on one or more database servers. The database management system may be a relational (RDBMS), hierarchical (HDBMS), multidimensional (MDBMS), object oriented (ODBMS or OODBMS) or object relational (ORDBMS) database management system. The data may, for example, be stored within a single relational database such as SQL Server from Microsoft Corporation. Although illustrated as local to client computer device 4, database 30 may be located remote from the client computing device and coupled to the client computing device via a public or private network, e.g., network 14.

Bracket data 32 describes a set of commercially-available brackets that may be selected by practitioner 8 and positioned within the 3D modeling environment. For example, bracket data 32 may store a variety of attributes for the commercially-available brackets, such as dimensions, slot locations and characteristics, torque angles, angulations and other attributes. User interface 22 provides a menu-driven interface by which practitioner 8 selects the type of brackets for use in defining a prescription for patient 6.

Patient data 36 describes a set of one or more patients, e.g., patient 6, associated with practitioner 8. For example, patient data 36 specifies general information, such as a name, birth date, and a dental history, for each patient. In addition, patient data 36 specifies a current prescription specified for each of the patients, including the types of brackets selected by practitioner 8 for use with each of the patients.

Planar guide data 42 specifies a variety of planar guides that may be selectively used by practitioner 8 to assist in precisely positioning and orienting the selected brackets. For example, practitioner 8 may elect to use one or more planar guides associated with the tooth on which the bracket is being placed. Two types of exemplary planar guides that may be selected by practitioner 8 include: (1) a mesial planar guide, and (2) a distal planar guide. These two planar guides are rendered parallel to and, optionally, equidistant from the midsagittal plane of the bracket being placed. A third type of planar guide is an occlusal planar guide that is rendered parallel to the midlateral plane or slot of the bracket and proximate to the occlusal surface of the tooth. A fourth type of planar guide is a gingival planar guide rendered parallel to the midlateral plane of the bracket and proximate to the gingival edge of the tooth.

Use of two or more of these planar guides allow practitioner 8 to precisely position and orient a bracket on a tooth by effectively "framing" the tooth. For example, practitioner 8 may either align the bracket with the tooth by aligning the mesial and distal planar guides parallel to the perceived midsagittal plane of the tooth or by aligning the occlusal planar guide with the desired occlusal plane of the dental arch.

Another exemplary type of planar guide is a midlateral planar guide that is rendered parallel to the midlateral plane of the bracket being placed. Similarly, a midfrontal planar guide may be rendered parallel to the midfrontal plane of the bracket, and a midsagittal planar guide may be rendered within a midsagittal plane of the bracket. Rather than being used to "frame" the tooth, however, the midlateral planar guide, midfrontal planar guide, and midsagittal planar guides may be useful in dissecting the tooth and visualizing cross-sections of the tooth. The intersection of the midsagittal plane and the facial surface of the tooth forms a curved line that is commonly known in the orthodontic industry as the Facial Axis of the Clinical Crown (FACC). The midsagittal planar guide can be used to aid practitioner 8 in identifying or visualizing this anatomical feature. Further, the intersection of the FACC and the midlateral plane forms a point that is commonly known as the Facial Axis Point or FA Point. Thus, together, the midsagittal planar guide and the midlateral planar guide can aid practitioner 8 in identifying the FA Point. Consequently, by utilizing the midlateral, midfrontal, and midsagittal planar guides, practitioner 8 may more easily place the orthodontic appliance on the tooth so that the occlusal-gingival axis of the appliance is aligned with the midsagittal plane or FACC, and the center of the base of the appliance is positioned over the FA Point.

In this manner, planar guide data 24 defines a variety of planar guides that may assist practitioner 8 in achieving proper appliance placement according to anatomical features of the teeth, which is often necessary for a prescription to achieve the desired results. Note that regardless of the specific planar guide or guides that may be used to assist practitioner 8 in achieving proper appliance placement, certain planar features of the teeth are often regarded as inherent to their anatomy. As a result, placement of appliances relative to these features can be subjective in nature. The application of planar guides as visual references and feedback devices, therefore, aids practitioner 8 in identifying these inherent anatomical features. Consequently, the planar guides described herein as being parallel to certain planes inherent to an orthodontic appliance will be parallel to their respective planes inherent to the anatomy of the tooth upon which the appliance is placed when practitioner 8 has placed or adjusted the appliance on the tooth in a manner deemed appropriate, such as that described above.

In addition to defining the available types of planar guides, planar guide data 42 stores attributes for the different types of planar guides. In particular, planar guide data 42 may store attributes for each type of planar guide with respect to different types of brackets or teeth within the dentition. Exemplary attributes include defined initial locations and distances relative to the tooth or other planar guides, enablement of gridlines, shear angles, scale, and other attributes.

Guide control module 24 creates a respective object with 3D data 34 for each type of planar guide enabled by practitioner 8. In one embodiment, guide control module 24 generates 3D data 34 to include a 1×1 unit-square object for each planar guide, and defines the attributes of the objects so that the object is displayed in one of a number of forms, e.g., semitransparent. Guide control module 24 may display the planar guides in other forms. For example, guide control module 24 may display different types of planar guides in different colors to contrast with each other and with the teeth of the patient. Guide control module 24 may adjust the color or transparency of each planar guide based on input from practitioner 8, and may render the planar guides opaque or invisible based on input from the practitioner. As another option, guide control module 24 may generate a planar guide as a partial plane comprising a series of lines (e.g., dashed or solid) that represent the plane without rendering the plane in its entirety.

In one embodiment, guide control module 24 generates the planar guides to include visual reference markers placed at discrete intervals in one or more dimensions where each interval is equal to a whole unit or fractional unit of measurement. For example, guide control module 24 may generate a planar guide to include a rectilinear grid of semi-transparent lines on one or more of the planar guides. The grid may be rendered at regular, discrete intervals, e.g., every millimeter, to allow visual measurements by practitioner 8. For example, depending on the type of planar guide, practitioner 8 may utilize the grid to visually measure the tooth, distances between brackets and various points around the perimeter of the tooth, distance between the bracket and the planar guides, and the like.

Other examples of visual reference markers include points, crosshairs, tic marks, discs, squares, or spheres placed at such discrete intervals. Such markers are not limited to the planes of the rendered planar guides. For example, guide control module 24 may generate the markers at cube corners throughout a volume bounded by the planar guides. Such markers might also be annotated with associated units of measurement.

In one embodiment, guide control module 24 generates the planar guides to include contour lines when the surface of a tooth or other object of examination either penetrates or lies proximal to a planar guide. These contour lines present circuits of constant distance or elevation of tooth or object features relative to the planar guide. Thus, the planar guide becomes a "map" indicating the magnitude of proximity of features relative to the plane. To visually indicate distance or elevation, guide control module 24 may render each contour in a color or grayscale or interrupted (dashed or dotted) line pattern according to a legend that defines the associated distance. Practitioner 8 may utilize this feature to gauge the proximity of a tooth, for example, relative to a planar guide when it is difficult or undesirable to reorient the viewpoint in the scene to otherwise visually gauge the proximity of the tooth. As a result, this feature allows practitioner 8 to position and orient brackets while maintaining a generally occlusal or gingival view of an arch, or some portion thereof, without repeatedly changing viewing perspective. In addition, this feature can also be used to form an "occlusal map" showing the proximity of individual cusps and fossae of teeth relative to an occlusal plane. Consequently, the contour lines can provide visual feedback in real-time in final occlusion mode as bracket positions and orientations are adjusted relative to their respective teeth, thus allowing practitioner 8 to set bracket positions and orientations to achieve a desired, functional, occlusion.

After creating each planar guide object within the 3D environment, guide control module 24 applies a 3D transformation to each planar guide. For example, the 3D transformation scales the object associated with the planar guide so that the planar guide is a proper size with respect to the tooth or dental arch with which the planar guide is associated. The 3D transformation may, for example, scale the planar guide so that its dimensions approximate the dimensions of the tooth.

In addition, the 3D transformation may shear the planar guide in accordance with a shear factor that is based on a tip or angulation associated with the bracket currently being placed. For example, the shear angles of a mesial planar guide and a distal planar guide may be set to conform to the occlusal-gingival axis of the bracket as it relates to the archwire slot. In this manner, the mesial and distal planar guides visibly align with the mesial and distal edges of the bracket, respectively, if the bracket was designed to exhibit edges that are parallel to one another and to the occlusal-gingival axis of the bracket. Alternately, or in addition to visible alignment with mesial and distal bracket edges, if the bracket exhibits an occlusal-gingival groove running along its midline for similar alignment purposes, the shear angles of a mesial planar guide and a distal planar guide may be set to conform to the occlusal-gingival groove as it relates to the archwire slot.

In this manner, guide control module 24 controls the location and orientation of the planar guide with the 3D environment based on planar guide data 42. In addition, guide control module 24 may further control the position and orientation of the planar guides to aid practitioner 8 in visually positioning and orienting each bracket in a manner that satisfies placement rules 40. Placement rules 40, for example, may specify industry-defined placement rules for commercially-available brackets. In addition, placement rules 40 may include user-defined rules specified by practitioner 8 or other rules for controlling bracket placement.

For example, one rule for certain commercially-available brackets is that the medial line or longitudinal axis of the bracket be aligned with the FACC of the tooth, lies in the midsagittal plane of the tooth as described above. To assist compliance with this rule, in one embodiment, guide control module 24 automatically controls the locations and orientations of the distal planar guide and the mesial planar guide as parallel to the midsagittal plane of the bracket currently being placed and equidistantly spaced from the medial line of a bracket. As practitioner 8 adjusts and orients the bracket, guide control module 24 automatically updates the distal and mesial planar guides. In this manner, the distal and mesial planar guides, and their relative distances to the distal and mesial surfaces of the tooth, assist practitioner 8 in positioning the bracket relative the midsagittal plane of the tooth in compliance with this rule.

Because different teeth have different mesiodistal widths, planar guide data 42 may store statistical normal distances for the width of each type of tooth for use in determining initial distances between the mesial and distal planar guides. User interface 22 may allow practitioner 8 to adjust planar guide data 42 to bias one or both of the mesial planar guide and the distal planar guide, thereby allowing the practitioner to more precisely identify the midsagittal plane of a tooth as correctly lying equidistant from the mesial and distal edges of the tooth. Guide control module 24 automatically updates planar guide data 42 as practitioner 8 adjusts the distance between the mesial and distal planar guides for each tooth. The ability to introduce such a bias to translate one or both of the mesial and distal planar guides may be useful in situations where a tooth is rotated in its socket and part of its facial surface is obscured near either the mesial or distal edge by another tooth, which may prevent a bracket from being placed in accordance with one or more commercial rules.

The mesial and distal planar guides need not necessarily lie perpendicular to the occlusal planar guide. For example, guide control module 24 may orient mesial and distal planar guides parallel to the midsagittal plane of the respective bracket, which is parallel to the longitudinal axis of the bracket. As a result, the angulation or tip inherent in the selected bracket for the tooth is reflected in the angle of deviation between a plane perpendicular to the occlusal plane of the dental arch of patient 6 and the midsagittal plane of the bracket. Such angulation or tip is similarly reflected in the inherent angles of the selected bracket. Having the angulation of the bracket selected for each tooth reflected in the angles between the planar guides allows practitioner 8 to align the bracket with the tooth by either aligning the mesial and distal planar guides with the perceived midsagittal plane of the tooth or by aligning the occlusal planar guide with the desired occlusal plane of the dental arch.

Another exemplary industry-defined placement rule is a requirement that the center of a base of the bracket be placed on the FACC of the tooth equidistant from the occlusal edge or occlusal-most point on the FACC and the gingival margin of the crown. As described above, this location is also known as the Facial Axis Point (FA Point). To assist compliance with this rule, in one embodiment, guide control module 24 automatically controls a gingival planar guide in conjunction with an occlusal planar guide to "frame" the tooth in a manner similar to that described above with respect to the mesial and distal planar guides. In this manner, practitioner 8 may more readily identify the FA Point midway between the gingival margin and the occlusal edge.

As another example, practitioner 8 may desire to place brackets a certain distance from the occlusal edge or occlusal most point on the FACC, rather than on the FA Point. Consequently, practitioner 8 may define one of placement rules 40 to direct guide control module 24 to place the occlusal planar guide parallel to the midlateral plane of the tooth at the defined distance from the center of the base of the bracket or the intended bracket location on the tooth. Practitioner 8 may define rules for different initial placement distances for different types of teeth in the dentition, for different types of brackets, or both. Optionally, the rules may be based in whole or in part on known rules associated with a particular type, or prescription, of the appliances selected by practitioner 8.

Rendering engine 26 accesses and renders 3D data 34 to generate the 3D view presented to practitioner 8 by user interface 22. More specifically, 3D data 34 includes information defining the 3D objects that represent each tooth, bracket, and planar guide within the 3D environment. Rendering engine 26 processes each object to render a 3D triangular mesh based on viewing perspective of practitioner 8 within the 3D environment. User interface 22 displays the rendered 3D triangular mesh to practitioner 8, and allows the practitioner to change viewing perspectives and manipulate objects within the 3D environment.

When the viewpoint or perspective of practitioner 8 is such that lines-of-sight from features on the tooth or other subject pass through two or more planar guides on their path to the viewpoint, rendering engine 26 computes the resultant pixel values on the viewplane associated with each line-of-sight. The application or choice of rendering method, in conjunction with selected planar guide colors, can be useful in indicating to practitioner 8 which planar guides lie in the line-of-sight of the practitioner and at what relative orientations. An exemplary formula may, for example, implement an additive or subtractive color model. In a subtractive color model, the planar guides tend to simulate physical sheets of light filter material, such as an acetate film that is dyed or coated with a certain color. As light passes through each film, all colors except the color of the film are removed from the spectrum. Therefore, two or more films of primary color can filter all of the light so that pixels in those lines-of-sight where overlap occurs will be relatively dark, if not black; however, the formulas can be adjusted to permit a certain percentage of ambient, diffuse, or other source of light to pass. In an additive color model, the films are treated more like contributors to the spectrum of the colors they represent. Therefore, overlapping films pass a broader spectrum of color than single films. An example is lines-of-sight that pass through red, green, and blue filters causing their respective pixels on the viewplane to be rendered white, assuming the light originating in the scene is white, such as light reflecting off a white tooth. In this manner, careful color selection of the planar guides by practitioner 8 and tuning of the rendering engine 26 can facilitate the practitioner's ability to determine relative positions and orientations of objects in 3D environment, including the viewpoint and location of the practitioner, the planar guides, and the subject.

Figure 3:
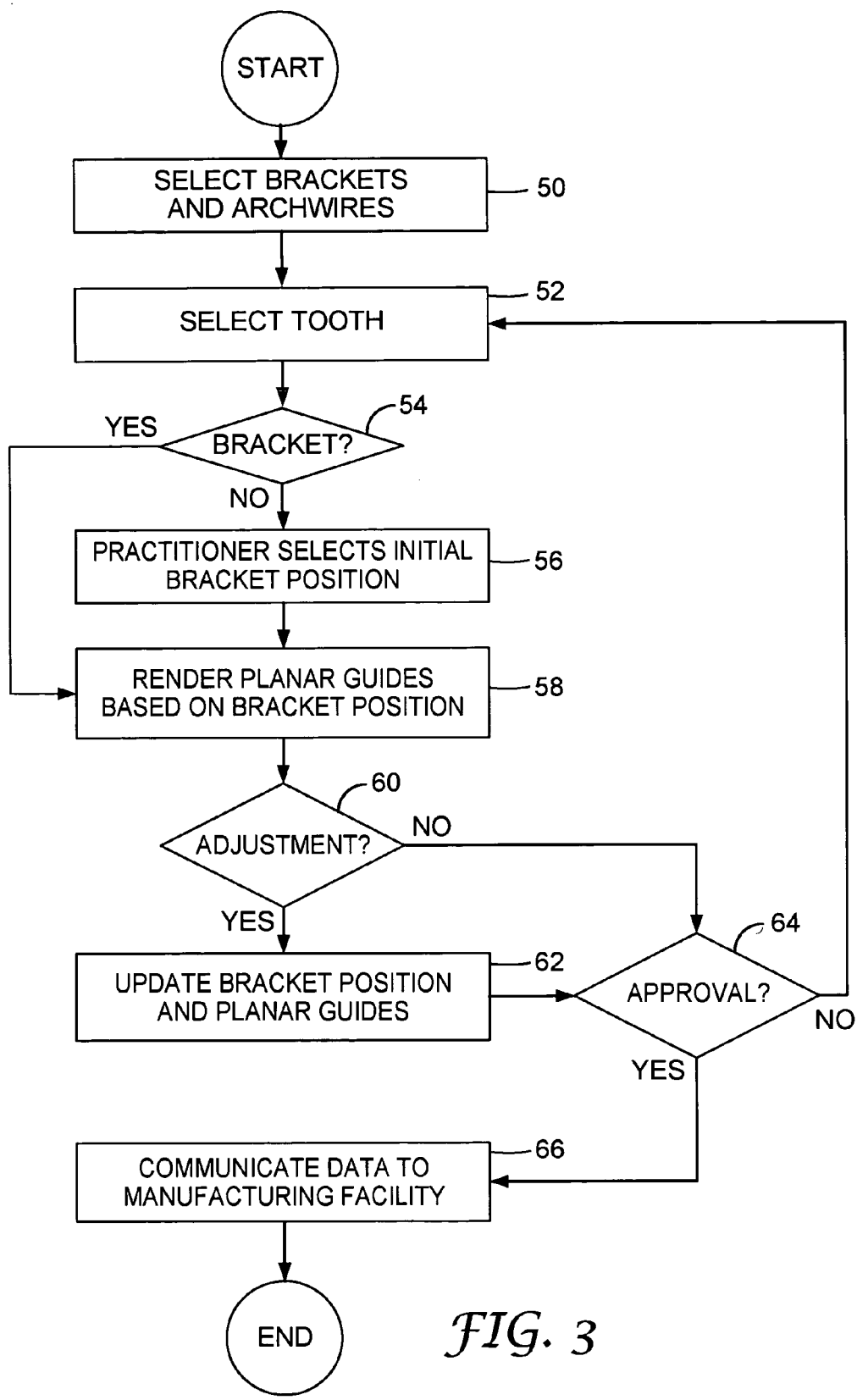
FIG. 3 is a flowchart illustrating exemplary operation of modeling software executing on the client computer device.

FIG. 3 is a flowchart illustrating an example operation of modeling software 20 executing on client computer device 4. More specifically, the flowchart of FIG. 3 illustrates operation of modeling software 20 in controlling and displaying planar guides within the 3D environment as visual aids to practitioner 8 when positioning and orienting orthodontic appliances, e.g., brackets.

Initially, modeling software 20 receives input from practitioner 8 and, based on the input, selects a set of commercially-available brackets that will be used for a prescription for patient 6 (50). To position a bracket within the 3D environment, modeling software 20 first receives input from practitioner 8 selecting one of the teeth within the modeled dental arch (52). If there is no bracket already positioned on the selected tooth, practitioner 8 interacts with modeling software 20 to select an initial bracket location (56). For example, practitioner 8 may simply click on an initial position of the tooth with a pointing device, e.g., a mouse. Alternatively, modeling software 20 may automatically select an initial bracket location based on placement rules 40, e.g., an industry-defined placement rule or a user-defined rule specified by practitioner 8 for initially locating the bracket.

Based on this initial location, modeling software 20 locates the bracket within the 3D environment, and renders one or more planar guides using a coordinate system associated with the bracket being placed (58). In response to input from practitioner 8 adjusting the position or orientation of the bracket with respect to the tooth (60), modeling software 20 automatically updates the positions and orientations of the bracket and any associated planar guides (62).

Practitioner 8 repeats this process of selecting teeth and placing and adjusting brackets on the teeth with the aid of planar guides until he or she is satisfied with the position and orientation of each bracket. Upon receiving approval from practitioner 8 (64), modeling software 20 communicates 3D data 34 to manufacturing facility 12 for fabrication of indirect bonding tray 16 based on the positions and orientations of the brackets selected by practitioner 8 (66).

Figure 4:
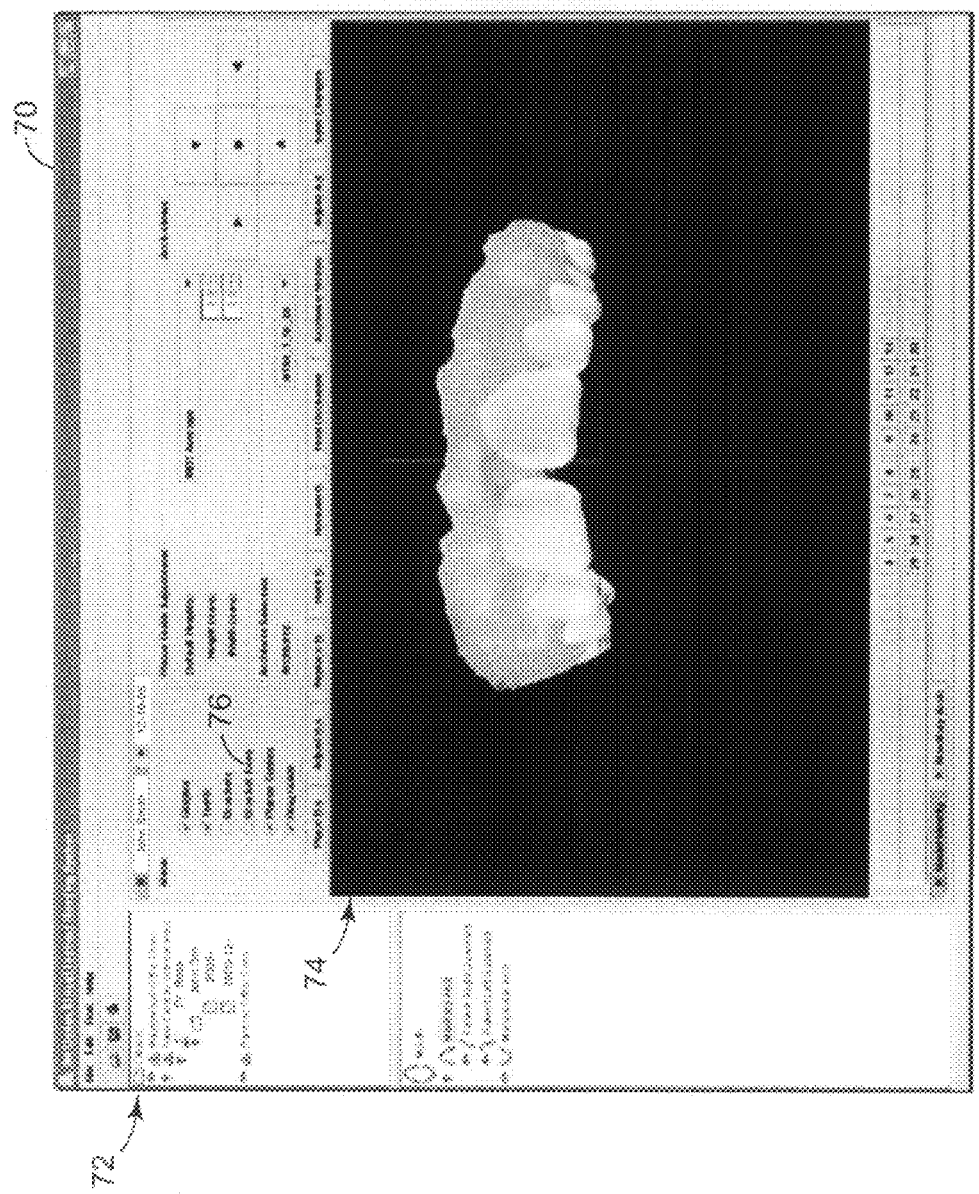
FIGS. 4-10 are display diagrams of an exemplary user interface presented by the modeling software.

FIGS. 4-16 are display diagrams illustrating exemplary graphical user interfaces (GUIs) presented by modeling software 20. For example, FIG. 4 illustrates an exemplary user interface 70. In the illustrated embodiment, user interface 70 includes a menu input area 72 by which a user, e.g., practitioner 8, accesses an electronic prescription for patient 6.

User interface 70 further includes display area 74 for presenting the 3D rendered representation of the teeth of patient 6. In this example, display area 74 presents a virtualized facial view of the malocclusal dental arch of patient 6. User interface 70 provides selection mechanism 76 by which practitioner 8 can selectively enable and disable the rendering and display of planar guides to assist positioning brackets within display area 74.

Figure 5:
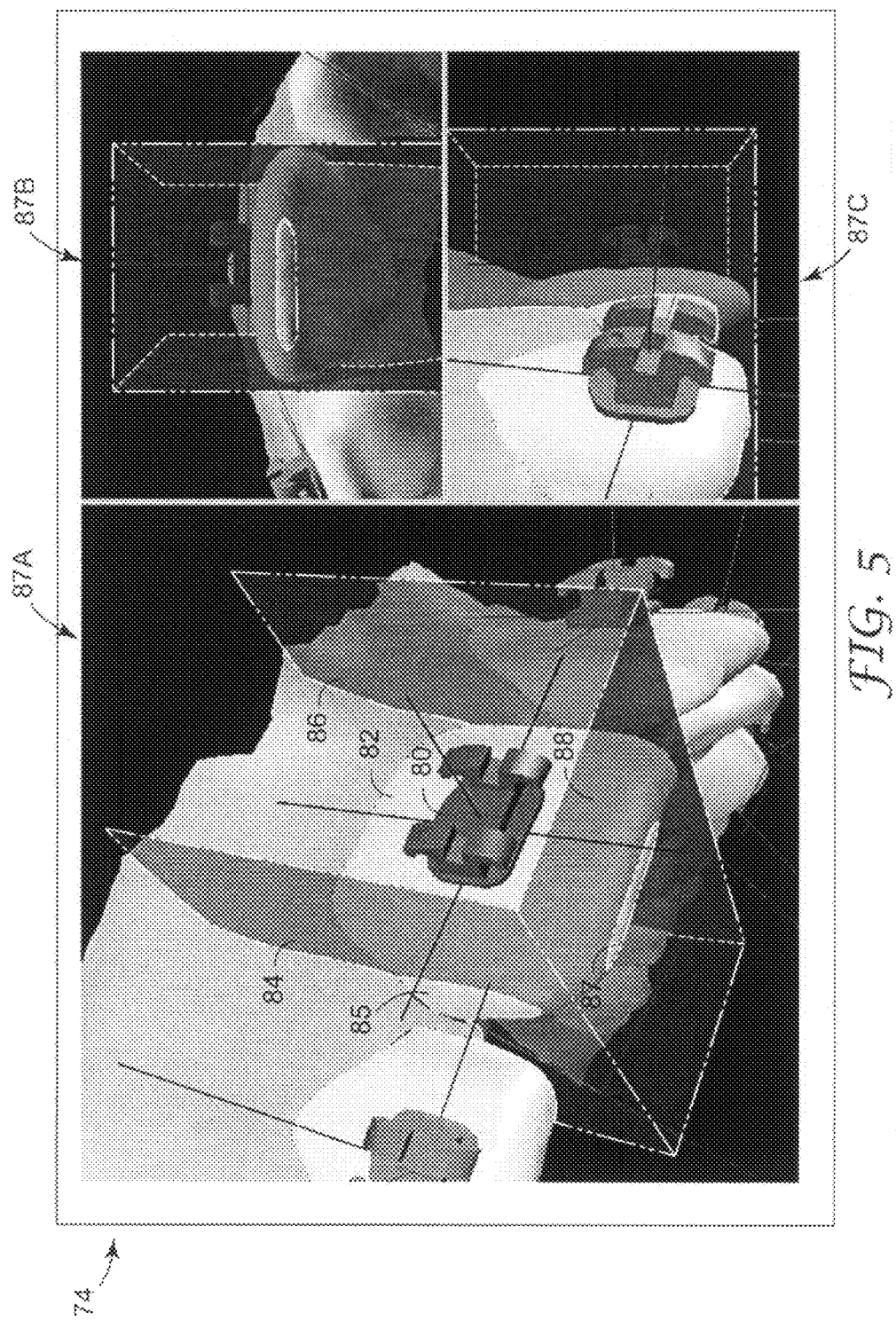

FIG. 5 illustrates an exemplary embodiment in which modeling software 20 places display area 74 into a bracket view mode having three viewing regions 87A, 87B and 87C. In this example, practitioner 8 has placed a bracket 80 on tooth 82 within the malocclusal dental arch. Viewing region 87A provides an expanded oblique view of the tooth 82, while viewing region 87C provides a zoomed or "close-up" view of the tooth. Viewing region 87B provides an occlusal view of tooth 82.

In addition, modeling software 20 has rendered and displayed a distal planar guide 84, a mesial planar guide 86, and an occlusal planar guide 88 within each of the viewing regions 87A-87C, allowing practitioner 8 to effectively frame tooth 82 and more easily position bracket 80. That is, modeling software 20 has displayed a distal planar guide 84, a mesial planar guide 86 and an occlusal planar guide 88 while also displaying the digital representation of tooth 82. As shown in FIG. 5, the planar guides are displayed separately from the digital representation of the tooth 82 within the 3D environment. The distal planar guide 84, mesial planar guide 86 and occlusal planar guide 88 lie in different planes within the 3D environment. In this example, distal planar guide 84 allows practitioner 8 to easily identify a portion 85 of the distal edge of tooth 82 penetrating the distal planar guide. Similarly, occlusal planar guide 88 allows practitioner 8 to easily identify a portion 87 of the occlusal surface of tooth 82 penetrating the occlusal planar guide.

Figure 6:
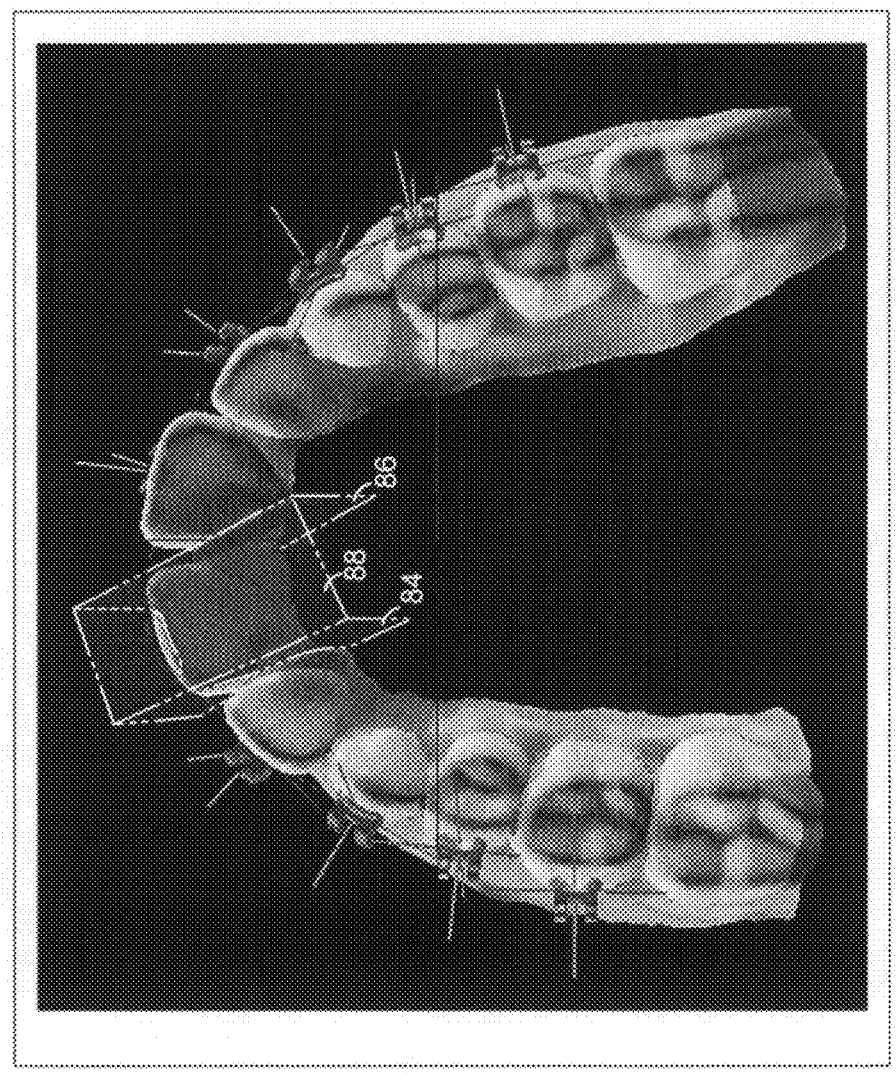

FIG. 6 illustrates an exemplary embodiment in which display area 74 provides an occlusal view of the malocclusal dental arch, including distal planar guide 84, mesial planar guide 86, and occlusal planar guide 88.

Figure 7:
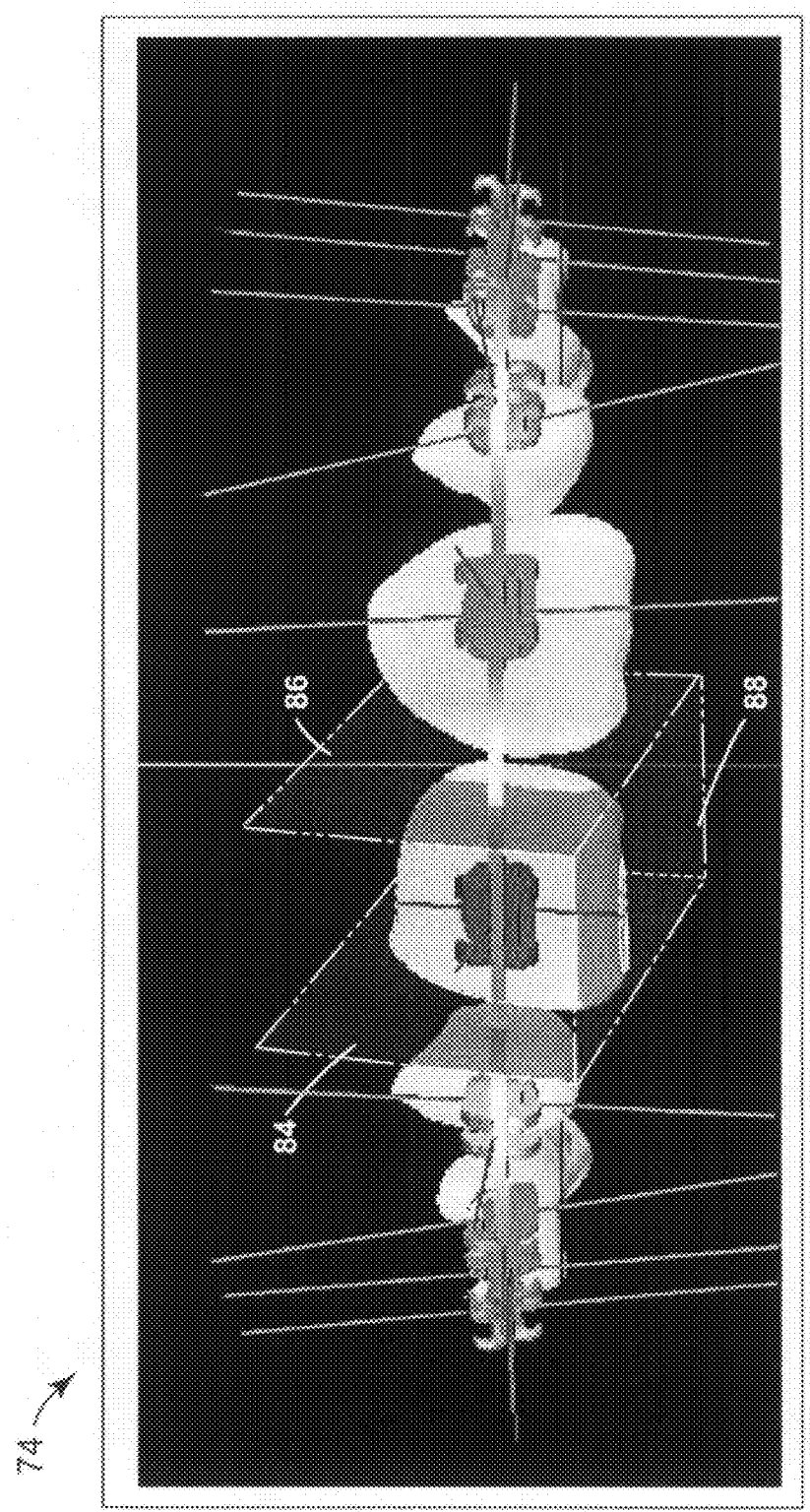

FIG. 7 illustrates an exemplary embodiment in which display area 74 provides a facial view of the dental arch in final occlusion without the gingiva. In other words, modeling software 20 displays the dental arch in post-treatment form based on the brackets and bracket positions selected for by practitioner 8. As illustrated, display area 74 presents distal planar guide 84, mesial planar guide 86, and occlusal planar guide 88 relative to the occlusal dental arch.

Figure 8:
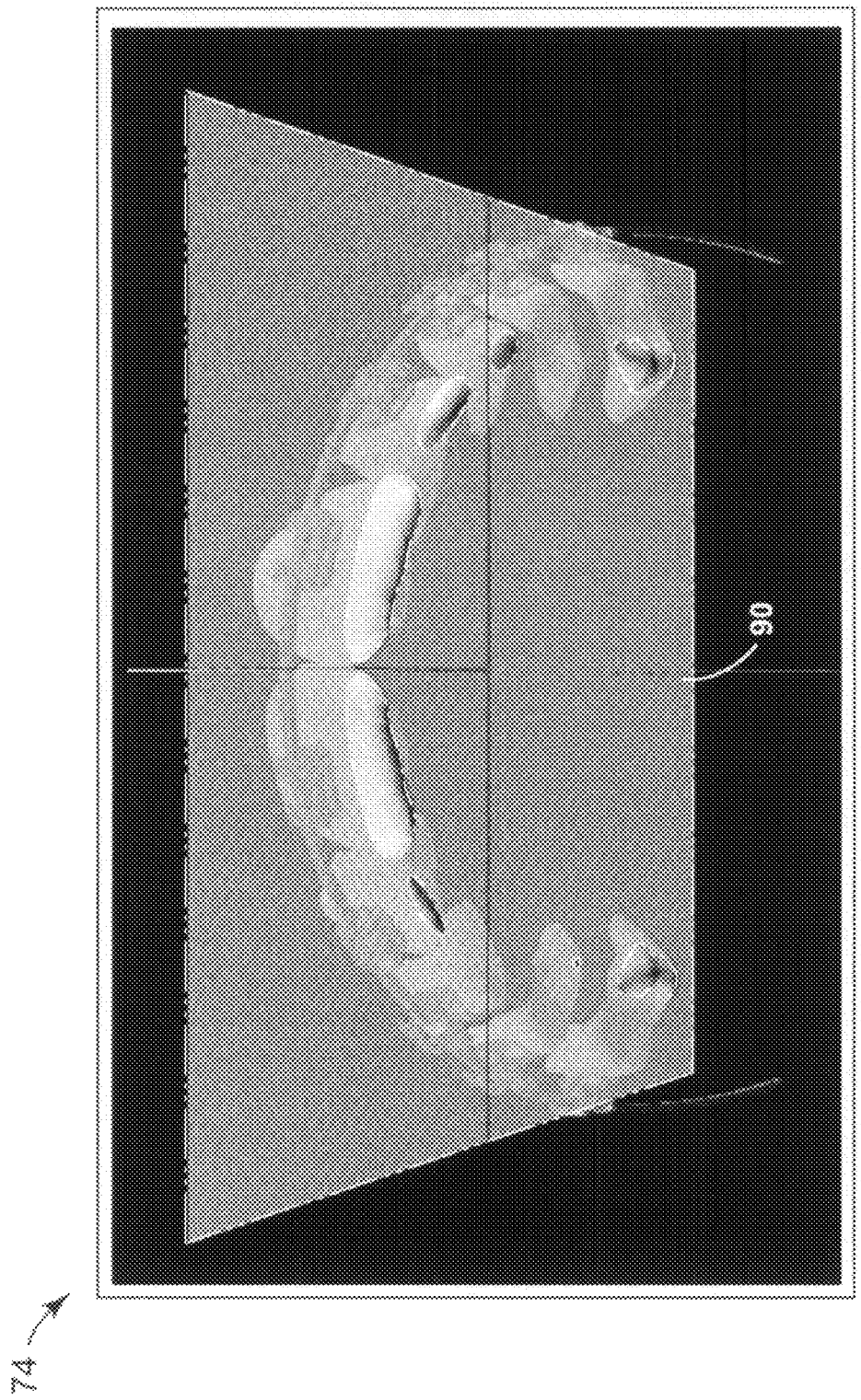

FIG. 8 illustrates an exemplary embodiment in which display area 74 provides an oblique view of the occlusal dental arch, and displays a final occlusal plane 90 to assist practitioner 8. Occlusal plane 90 allows practitioner 8 to visually assess the alignment of the post-treatment teeth positions relative to occlusal plane 90. In the example, practitioner 8 is also able to visually assess the extent that certain teeth penetrate occlusal plane 90. Alternatively, occlusal plane 90 may be rendered together with the pre-treatment or malocclusal arch to visually assess the alignment of the pre-treatment or malocclusal teeth positions relative to the occlusal plane 90.

Figure 9:
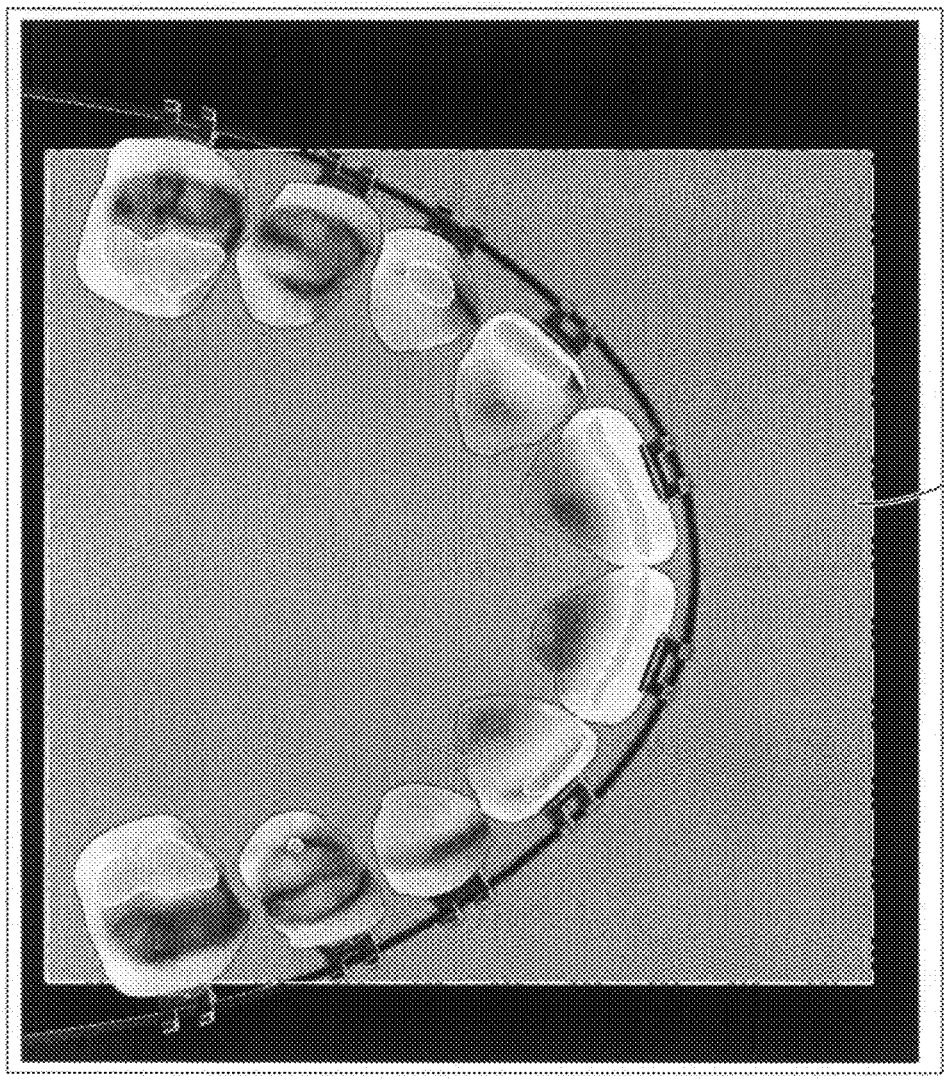

FIG. 9 illustrates an exemplary embodiment in which display area 74 provides a gingival view of the occlusal dental arch including final occlusal plane 90.

Figure 10:
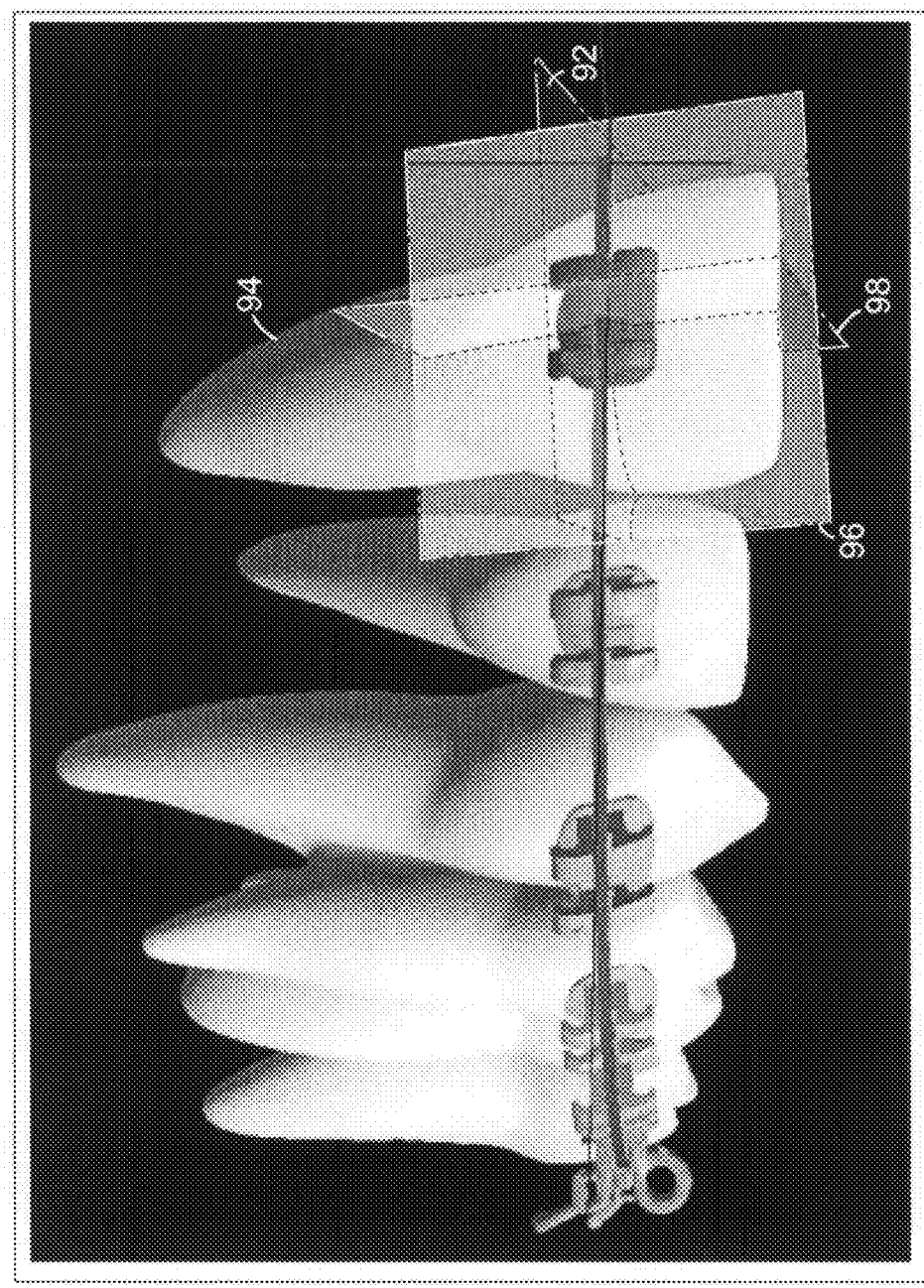

FIG. 10 illustrates an exemplary embodiment in which display area 74 provides an oblique view of the occlusal dental arch. In this embodiment, display area 74 presents a midlateral planar guide 92 that is rendered within the midlateral plane of tooth 94. In addition, display area 74 presents a midfrontal planar guide 96 rendered parallel to a midfrontal plane of tooth 94, and a midsagittal planar guide 98 rendered within a midsagittal plane of tooth 94.

For exemplary purposes, the techniques described herein have been illustrated in reference to assisting a practitioner with the placement and orientation of orthodontic brackets. However, the techniques may readily be applied to positioning and orienting other types of orthodontic appliances relative to teeth or other regions of a dental arch. For example, the techniques may readily be used to assist a practitioner in placing, positioning, forming or otherwise designing a wide variety of appliances, such as buccal tubes, buttons, sheaths, arch wires, and other orthodontic appliances. Consequently, the term orthodontic appliance is generally used herein to refer to a device, either fixed to the teeth or removable, that applies force to the teeth and their supporting structures to produce changes in their relationship to each other and to control their growth and development.

Moreover, the described techniques may be utilized to apply planar guides to the anatomy of an individual tooth or to an entire dentition. In the case of an entire dentition, the occlusal plane would be analogous to the midlateral plane of the patient's mouth. As the mouth also has a midfrontal plane and a midsagittal plane, these types of planar guides may aid the general diagnosis of a patient's malocclusion, including determination of a patient's arch form. Similarly, these planar guides can be used as visual references in the modification of standard archwire forms or the design of custom archwire forms. Further, such planar guides might be applied more generally to the diagnosis of craniofacial misalignments or the alignment of a patient's dentition relative to surrounding craniofacial structures. Other applications include, but are not limited to, computer-aided attachment, adjustment, or design of peripheral headgear or other such appliances used in orthodontic treatment.

Various implementations and embodiments of the invention have been described. Nevertheless, it is understood that various modifications can be made without departing from the invention. These and other embodiments are within the scope of the following claims.

The invention claimed is:

1. A method comprising:
    displaying, via a user interface of a computing device, a three-dimensional (3D) digital representation of a tooth of a dental arch within a 3D environment;
    while displaying the digital representation of the tooth of the dental arch, displaying, via the user interface of the computing device, a two-dimensional planar guide within the 3D environment as a visual aid to a practitioner in a placement of an orthodontic appliance relative to the tooth of the dental arch within the 3D environment, the planar guide having a planar guide orientation within the 3D environment and
    computing the planar guide orientation of the planar guide based on the placement of the orthodontic appliance within the 3D environment relative to the dental arch,
    wherein the two-dimensional planar guide is displayed separately from the digital representation of the tooth, and
    wherein displaying the planar guide comprises, as the practitioner moves the orthodontic appliance relative to the tooth within the 3D environment, rendering the planar guide at a location that is based on at least one of a position or an orientation of the orthodontic appliance within the 3D environment.

2. The method of claim 1, wherein displaying a planar guide comprises displaying the planar guide proximal to a surface of the digital representation of the tooth of the dental arch to aid the practitioner in the placement of the orthodontic appliance on the tooth.

3. The method of claim 2, wherein displaying a planar guide further comprises generating the planar guide within the 3D environment relative to a coordinate system associated with the orthodontic appliance.

4. The method of claim 1, wherein the planar guide comprises a mesial planar guide, and displaying a planar guide further comprises rendering the mesial planar guide and a distal planar guide parallel to a midsagittal plane of the orthodontic appliance, wherein the orthodontic appliance defines a mesial edge, a distal edge, and a longitudinal axis and the midsagittal plane is substantially parallel to the longitudinal axis, and wherein the mesial planar guide aligns with the mesial edge of the orthodontic appliance and the distal planar guide aligns with the distal edge of the orthodontic appliance.

5. The method of claim 4, wherein rendering a mesial planar guide and a distal planar guide further comprises rendering the mesial planar guide and the distal planar guide parallel to and equidistant from the midsagittal plane of the orthodontic appliance.

6. The method of claim 1, wherein the planar guide comprises an occlusal planar guide, and displaying a planar guide further comprises rendering the occlusal planar guide parallel to a midlateral plane of the orthodontic appliance and proximate an occlusal surface of the tooth of the dental arch.

7. The method of claim 1, wherein the planar guide comprises a midlateral planar guide, and displaying a planar guide further comprises rendering the midlateral planar guide parallel to a midlateral plane of the orthodontic appliance.

8. The method of claim 1, wherein the planar guide comprises a midfrontal planar guide, and displaying a planar guide further comprises rendering the midfrontal planar guide parallel to a midfrontal plane of the orthodontic appliance.

9. The method of claim 1, wherein the planar guide comprises a midsagittal planar guide, and displaying a planar guide further comprises rendering the midsagittal planar guide parallel to a midsagittal plane of the orthodontic appliance, wherein the midsagittal plane is substantially parallel to a longitudinal axis of the orthodontic appliance.

10. The method of claim 1, wherein the planar guide comprises a gingival planar guide, and displaying a planar guide further comprises rendering the gingival planar guide parallel to a midlateral plane of the orthodontic appliance and proximate a gingival edge of the tooth of the dental arch.

11. The method of claim 1, wherein displaying a planar guide further comprises displaying the planar guide as a semi-transparent two-dimensional plane within the 3D environment.

12. The method of claim 1, wherein displaying a planar guide further comprises displaying the planar guide as a partial plane comprising at least two lines within the 3D environment.

13. The method of claim 1, further comprising:
displaying, via the user interface of the computing device, the planar guide as a first planar guide having a first color; and
displaying, via the user interface of the computing device, a second planar guide within the 3D environment with a second color different from the first color.

14. The method of claim 13, further comprising adjusting the first color and the second color in response to input from the practitioner.

15. The method of claim 1, further comprising adjusting a transparency of the planar guide based on input from the practitioner.

16. The method of claim 1, further comprising displaying the planar guide as opaque or invisible based on input from the practitioner.

17. The method of claim 1, further comprising:
storing data with the computing device, wherein the data describes attributes for types of orthodontic appliances that may be selected by the practitioner, and
controlling the display of the planar guide based on the stored attributes for the types of orthodontic appliances.

18. The method of claim 17, wherein storing attributes for types of orthodontic appliances comprises storing one or more of dimensions, slot locations, torque angles, and angulations for the types of orthodontic appliances.

19. The method of claim 1, further comprising:
storing planar guide data with the computing device, wherein the planar guide data specifies a plurality of types of planar guides;
receiving input from the practitioner enabling the display of at least one or more the types of planar guides; and
displaying the planar guide via the user interface in accordance with the selected one or more types of planar guides.

20. The method of claim 1, further comprising:
storing planar guide data with the computing device, wherein the planar guide data describes attributes for different types of planar guides, and
displaying the planar guide via the user interface in accordance with the stored attributes for the different types of planar guides.

21. The method of claim 20, wherein storing planar guide data comprises storing attributes for the different types of planar guides with respect to different types of orthodontic appliances.

22. The method of claim 20, wherein storing planar guide data comprises storing attributes for the different types of planar guides with respect to different types of teeth within the dental arch.

23. The method of claim 20, wherein storing planar guide data comprises storing attributes that specify distances for each of the different types of planar guides with respect to at least one of the tooth of the dental arch, a different one of the planar guides, and the orthodontic appliance.

24. The method of claim 20, wherein storing planar guide data comprises storing attributes that specify shear angles and scales for the different types of planar guides.

25. The method of claim 1, further comprising automatically scaling the planar guide within the 3D environment to size the planar guide based on one or more dimensions of the tooth of the dental arch.

26. The method of claim 1, further comprising automatically shearing the planar guide in accordance with a shear factor that is based on an angulation associated with the orthodontic appliance.

27. The method of claim 26, wherein the orthodontic appliance defines a mesial edge and a distal edge, and wherein automatically shearing the planar guide comprises automatically shearing the planar guide to align the planar guide with at least one of the mesial edge or the distal edge of the orthodontic appliance.

28. The method of claim 1, further comprising:
storing data with the computing device, wherein the data defines one or more placement rules for placing the orthodontic appliance; and
controlling the planar guide to assist the practitioner in positioning the orthodontic appliance in accordance with the placement rules.

29. The method of claim 28, further comprising automatically rendering the planar guide within the 3D environment as parallel to a midsagittal plane of the orthodontic appliance in response to one of the placement rules that requires a longitudinal or occlusal-gingival axis of the orthodontic appliance be aligned with a midsagittal plane of the tooth, wherein the midsagittal plane of the orthodontic appliance is substantially parallel to the longitudinal axis of the orthodontic appliance.

30. The method of claim 1, further comprising:
storing, with the computing device, statistical normal distances for one or more dimensions of teeth; and
rendering the planar guide at the location within the 3D environment based on the statistical normal distances.

31. The method of claim 30, further comprising:
receiving input biasing the planar guide relative to the statistical normal distance; and
adjusting the location for the planar guide within the 3D environment based on the input.

32. The method of claim 1, further comprising displaying, via the user interface of the computing device, visual reference markers relative to the planar guide at discrete intervals.

33. The method of claim 32, wherein displaying visual reference markers comprises displaying a rectilinear grid of semi-transparent lines on the planar guide.

34. The method of claim 32, wherein displaying visual reference markers comprises displaying points, crosshairs, tic marks, discs, squares, or spheres at the discrete intervals.

35. The method of claim 32, wherein displaying visual reference markers comprises displaying the visual reference markers throughout a volume bounded by the planar guide and at least one other planar guide.

36. The method of claim 1, further comprising displaying, via the user interface of the computing device, contour lines on the planar guide, wherein each contour line indicates a constant distance to a surface of the tooth within the 3D environment relative to the planar guide.

37. The method of claim 1, wherein the orthodontic appliance comprises an orthodontic bracket, a buccal tube, a sheath, a button or an arch wire.

38. The method of claim 1, wherein the planar guide comprises a first planar guide, the method further comprising:
while displaying the digital representation of the tooth of the dental arch and the first planar guide, displaying, via the user interface of the computing device, a second two-dimensional planar guide within the 3D environment, wherein the first and second planar guides lie in different planes.

39. The method of claim 38, further comprising automatically moving the first planar guide and the second planar guide within the 3D environment as the practitioner moves the orthodontic appliance with respect to the tooth within the 3D environment.

40. The method of claim 1, wherein the planar guide comprises an occlusal planar guide, and displaying a planar guide further comprises rendering the occlusal planar guide to penetrate an occlusal surface of the digital representation of the tooth.

41. The method of claim 1, wherein the planar guide comprises a distal planar guide, and displaying a planar guide further comprises rendering the distal planar guide to penetrate a distal edge of the digital representation of the tooth.

42. The method of claim 1, wherein displaying the two-dimensional planar guide comprises displaying at least one two-dimensional planar guide that does not contact the orthodontic appliance within the 3D environment.

43. The method of claim 1, further comprising:
receiving user input adjusting a distance between the planar guide and the orthodontic appliance, wherein displaying the planar guide within the 3D environment comprises displaying the planar guide at the distance from the orthodontic appliance within the 3D environment.

44. The method of claim 1, wherein the planar guide comprises a first planar guide and the location comprises a first location, the method further comprising, while displaying the digital representation of the tooth of the dental arch, displaying, via the user interface of the computing device, a second two-dimensional planar guide within the 3D environment, wherein displaying the second planar guide comprises, as the practitioner moves the orthodontic appliance relative to the tooth within the 3D environment, rendering the second planar guide at a second location that is based on at least one of the position or the orientation of the orthodontic appliance within the 3D environment, wherein a distance between the first and second planar guides within the 3D environment is adjustable.

45. A method comprising:
displaying, via a user interface of a computing device, a three-dimensional (3D) digital representation of a tooth of a dental arch within a 3D environment;
positioning an orthodontic appliance at a position within the 3D environment in response to input from a practitioner;
while displaying the digital representation of the tooth of the dental arch, displaying, via the user interface of the computing device, a two-dimensional planar guide within the 3D environment as a visual aid to the practitioner in a placement of the orthodontic appliance relative to the tooth of the dental arch within the 3D environment, the planar guide having a planar guide orientation within the 3D environment, wherein the two-dimensional planar guide is displayed separately from the digital representation of the tooth; and
computing the planar guide orientation of the planar guide based on the placement of the orthodontic appliance within the 3D environment relative to the dental arch, and
wherein displaying the planar guide comprises:
rendering the planar guide at a location within the 3D environment that is based on the position of the orthodontic appliance;
receiving input from the practitioner moving the placement of the orthodontic appliance with respect to the tooth within the 3D environment; and
automatically moving the planar guide within the 3D environment as the practitioner moves the orthodontic appliance with respect to the tooth within the 3D environment.

46. A system comprising:
a computing device; and
modeling software executing on the computing device, wherein the modeling software comprises:
a rendering engine that renders a three-dimensional (3D) digital representation of a tooth of a dental arch within a 3D environment;
a user interface that displays the digital representation of the tooth of the dental arch while displaying a two-dimensional planar guide within the 3D environment as a visual aid to a practitioner in a placement of an orthodontic appliance relative to the dental arch within the 3D environment, wherein the planar guide is displayed separately from the digital representation of the tooth, and wherein, as the practitioner moves the orthodontic appliance relative to the tooth within the 3D environment, the rendering engine renders the planar guide at a location based on at least one of a position or an orientation of the orthodontic appliance within the 3D environment and
a guide control module that computes a planar guide orientation of the planar guide within the 3D environment based on the placement of the orthodontic appliance within the 3D environment relative to the dental arch.

47. The system of claim 46, wherein the guide control module controls the location of the planar guide within the 3D environment.

48. The system of claim 47, wherein the guide control module locates the planar guide proximate to a surface of the digital representation of the tooth of the dental arch within the 3D environment to aid the practitioner in adjusting the placement of the orthodontic appliance on the tooth.

49. The system of claim 47, wherein the guide control module generates the planar guide within the 3D environment based on a coordinate system associated with the orthodontic appliance.

50. The system of claim 47, wherein the guide control module receives input from the practitioner via the user interface, the input comprising an adjustment to the placement of the orthodontic appliance with respect to the tooth within the 3D environment, and automatically moves the planar guide within the 3D environment as the practitioner moves the orthodontic appliance with respect to the tooth within the 3D environment.

51. The system of claim 47, wherein the planar guide comprises a mesial planar guide, and the guide control module generates the mesial planar guide and a distal planar guide parallel to a midsagittal plane of the orthodontic appliance, wherein the orthodontic appliance defines a mesial edge, a distal edge, and the midsagittal plane is substantially parallel to a longitudinal axis of the orthodontic appliance and aligns with the mesial edge of the orthodontic appliance and the distal planar guide aligns with the distal edge of the orthodontic appliance.

52. The system of claim 51, wherein the guide control module generates the mesial planar guide and the distal planar guide parallel to and equidistant from the midsagittal plane of the orthodontic appliance.

53. The system of claim 47, wherein the planar guide comprises an occlusal planar guide, and the guide control module locates the occlusal planar guide within the 3D environment parallel to a midlateral plane of the orthodontic appliance and proximate an occlusal surface of the tooth.

54. The system of claim 47, wherein the planar guide comprises a midlateral planar guide, and the guide control module locates the midlateral planar guide parallel to a midlateral plane of the appliance.

55. The system of claim 47, wherein the planar guide comprises a midfrontal planar guide, and the guide control module generates the midfrontal planar guide parallel to a midfrontal plane of the orthodontic appliance within the 3D environment.

56. The system of claim 47, wherein the planar guide comprises a midsagittal planar guide, and the guide control module generates the midsagittal planar guide parallel to a midsagittal plane of the orthodontic appliance, wherein the midsagittal plane is substantially parallel to a longitudinal axis of the orthodontic axis.

57. The system of claim 47, wherein the planar guide comprises a gingival planar guide, and displaying a planar guide further comprises rendering the gingival planar guide parallel to a midlateral plane of the orthodontic appliance and proximate a gingival edge of the tooth.

58. The system of claim 47, further comprising:
a database that stores data that describes attributes for types of orthodontic appliances that may be selected by the practitioner, and
wherein the guide control module controls the location of the planar guide based on the stored attributes.

59. The system of claim 58, wherein the database is located remote from the computing device and coupled to the computing device via a network.

60. The system of claim 58, wherein the attributes comprise one or more of dimensions, slot locations, torque angles, and angulations for the types of orthodontic appliances.

61. The system of claim 47, further comprising:
a database that stores planar guide data that specifies a plurality of types of planar guides,
wherein the user interface receives input from the practitioner enabling the display of at least one or more of the types of planar guides, and the guide control module controls the planar guide within the 3D environment in accordance with the selected one or more types of planar guides.

62. The system of claim 47, further comprising:
a database that stores planar guide data that describes attributes for different types of planar guides, and
wherein the guide control module controls the planar guide within the 3D environment in accordance with the stored attributes for the different types of planar guides.

63. The system of claim 62, wherein the database stores attributes for the different types of planar guides with respect to different types of orthodontic appliances.

64. The system of claim 62, wherein the database stores attributes for the different types of planar guides with respect to different types of teeth within the dental arch.

65. The system of claim 62, wherein the database stores attributes that specify distances for each of the different types of planar guides with respect to at least one of the tooth of the dental arch, a different one of the planar guides, and the orthodontic appliance.

66. The system of claim 62, wherein the database stores attributes that specify shear angles and scales for the different types of planar guides.

67. The system of claim 47, wherein the guide control module automatically scales the planar guide within the 3D environment to size the planar guide based on one or more dimensions of the tooth within the dental arch.

68. The system of claim 47, wherein the guide control module automatically shears the planar guide in accordance with a shear factor that is based on an angulation associated with the orthodontic appliance.

69. The system of claim 47, the orthodontic appliance defines a mesial edge and a distal edge, and wherein the guide control module automatically shears the planar guide in accordance with an angle of the orthodontic appliance to align the planar guide with at least one of the mesial edge or the distal edge of the orthodontic appliance.

70. The system of claim 47, further comprising
a database that stores data defining one or more placement rules for placing the orthodontic appliance, and
wherein the guide control module controls the planar guide within the 3D environment in accordance with the placement rules.

71. The system of claim 70, wherein the guide control module automatically renders the planar guide within the 3D environment as parallel to a midsagittal plane of the orthodontic appliance in response to one of the placement rules that requires a longitudinal axis or an occlusal-gingival axis of the orthodontic appliance be aligned with the midsagittal plane of the tooth.

72. The system of claim 47, further comprising:
a database that stores statistical normal distances for one or more dimensions of teeth, and
wherein the guide control module controls the location of the planar guide within the 3D environment based on the statistical normal distances.

73. The system of claim 47, wherein the user interface receives input biasing the planar guide relative to the statistical normal distance, and the guide control module adjusts the location for the planar guide based on the input.

74. The system of claim 46, wherein the user interface displays the planar guide as a semi-transparent two-dimensional plane within the 3D environment.

75. The system of claim 46, wherein the user interface displays the planar guide as a partial plane comprising at least two lines.

76. The system of claim 46, wherein the user interface displays visual reference markers relative to the planar guide at discrete intervals.

77. The system of claim 76, wherein the user interface displays the visual reference markers as a rectilinear grid of semi-transparent lines on the planar guide.

78. The system of claim 76, wherein the user interface displays the visual reference markers as points, crosshairs, tic marks, discs, squares, or spheres at the discrete intervals.

79. The system of claim 76, wherein the user interface displays the visual reference markers throughout a volume bounded by the planar guide and at least one other planar guide.

80. The system of claim 46, wherein the user interface displays contour lines on the planar guide, wherein each contour line indicates a constant distance to a surface of the tooth within the 3D environment relative to the planar guide.

81. The system of claim 46, wherein the orthodontic appliance comprises an orthodontic bracket, a buccal tube, a sheath, a button or an arch wire.

82. The system of claim 46, wherein the planar guide comprises an occlusal planar guide that penetrates an occlusal surface of the digital representation of the tooth.

83. The system of claim 46, wherein the planar guide comprises a distal planar guide that penetrates a distal edge of the digital representation of the tooth.

84. A non-transitory computer-readable medium comprising instructions for causing a programmable processor to:
   render a three-dimensional (3D) digital representation of a tooth within the 3D environment;
   while displaying the digital representation of the tooth, display a two-dimensional planar guide within the 3D environment as a visual aid to a practitioner in a placement of an orthodontic appliance relative to the tooth within the 3D environment, the planar guide having a planar guide orientation within the 3D environment, wherein the planar guide is displayed separately from the digital representation of the tooth, and wherein the instructions cause the programmable processor to display the planar guide by rendering the planar guide at a location based on a position of the orthodontic appliance within the 3D environment as the practitioner moves the orthodontic appliance relative to the tooth within the 3D environment; and
   compute the planar guide orientation of the planar guide based on the placement of the orthodontic appliance within the 3D environment relative to the dental arch.

85. The non-transitory computer-readable medium of claim 84, wherein the instructions cause the processor to:
   associate a coordinate system with the orthodontic appliance within the 3D environment, and
   generate the planar guide within the 3D environment relative to the coordinate system associated with the orthodontic appliance.

86. The non-transitory computer-readable medium of claim 84, wherein the instructions cause the processor to receive input from the practitioner via the user interface, the input comprising an adjustment to the placement of the orthodontic appliance with respect to the tooth within the 3D environment, and automatically move the planar guide within the 3D environment as the practitioner adjusts the placement of the orthodontic appliance with respect to the tooth within the 3D environment.

87. The non-transitory computer-readable medium of claim 84, wherein the instructions cause the processor to display the planar guide as one of:
   a mesial planar guide or a distal planar guide parallel to and optionally equidistant from a midsagittal plane of the orthodontic, wherein the orthodontic appliance defines a mesial edge, a distal edge, and a longitudinal axis and the midsagittal plane is substantially parallel to the longitudinal axis, and wherein the mesial planar guide aligns with the mesial edge of the orthodontic appliance and the distal planar guide aligns with the distal edge of the orthodontic appliance,
   an occlusal planar guide parallel to a midlateral plane of the orthodontic appliance and proximate an occlusal surface of the tooth,
   a gingival planar guide parallel to a gingival edge of the orthodontic appliance,
   a midlateral planar guide parallel to a midlateral plane of the orthodontic appliance,
   a midfrontal planar guide parallel to a midfrontal plane of the orthodontic appliance, and
   a midsagittal planar guide parallel to the midsagittal plane of the orthodontic appliance.

88. The non-transitory computer-readable medium of claim 84, wherein the instructions cause the processor to:
   store data defining one or more placement rules for placing the orthodontic appliance; and
   control the planar guide to assist the practitioner in positioning the orthodontic appliance in accordance with the placement rules.

89. The non-transitory computer-readable medium of claim 84, wherein the planar guide comprises at least one of an occlusal planar guide that penetrates an occlusal surface of the digital representation of the tooth or a distal planar guide that penetrates a distal edge of the digital representation of the tooth.

* * * * *

UNITED STATES PATENT AND TRADEMARK OFFICE
CERTIFICATE OF CORRECTION

PATENT NO. : 8,194,067 B2  
APPLICATION NO. : 10/771641  
DATED : June 5, 2012  
INVENTOR(S) : Richard E Raby Page 1 of 1

It is certified that error appears in the above-identified patent and that said Letters Patent is hereby corrected as shown below:

Column 12
Line 13, Claim 1, delete "environment" and insert -- environment; --, therefor.

Column 13
Line 38, Claim 18, delete "storing" and insert -- storing data that describes --, therefor.
Line 47, Claim 19, delete "more" and insert -- more of --, therefor.

Column 16
Line 4, Claim 45, after "arch," delete "and".
Line 35, Claim 46, delete "environment" and insert -- environment; --, therefor.

Signed and Sealed this
Fourteenth Day of August, 2012

David J. Kappos
*Director of the United States Patent and Trademark Office*